(12) United States Patent
Peltola et al.

(10) Patent No.: US 9,974,975 B2
(45) Date of Patent: May 22, 2018

(54) METHOD AND APPARATUS FOR USING PREFERRED ANGLES WHEN IRRADIATING PATIENT TARGET VOLUMES

(71) Applicant: Varian Medical Systems International AG, Cham (CH)

(72) Inventors: Jarkko Peltola, Tuusula (FI); Janne Nord, Espoo (FI)

(73) Assignee: Varian Medical Systems International AG, Cham (CH)

( * ) Notice: Subject to any disclaimer, the term of this patent is extended or adjusted under 35 U.S.C. 154(b) by 1120 days.

(21) Appl. No.: 14/039,883

(22) Filed: Sep. 27, 2013

(65) Prior Publication Data

US 2014/0275701 A1  Sep. 18, 2014

Related U.S. Application Data

(60) Provisional application No. 61/784,110, filed on Mar. 14, 2013.

(51) Int. Cl.
*A61N 5/10* (2006.01)

(52) U.S. Cl.
CPC .......... *A61N 5/1001* (2013.01); *A61N 5/1031* (2013.01); *A61N 5/1038* (2013.01); *A61N 5/1047* (2013.01); *A61N 5/1048* (2013.01); *A61N 5/1064* (2013.01)

(58) Field of Classification Search
CPC .......... A61N 5/1049; A61N 2005/1091; A61N 5/1042; A61N 5/10; A61N 5/103; A61N 5/1031; A61N 5/1048
See application file for complete search history.

(56) References Cited

U.S. PATENT DOCUMENTS

| | | | |
|---|---|---|---|
| 2006/0274885 A1 | 12/2006 | Wang et al. | |
| 2008/0242914 A1 | 10/2008 | Henderson et al. | |
| 2010/0322381 A1* | 12/2010 | Stahl | A61N 5/103 378/65 |
| 2012/0136194 A1* | 5/2012 | Zhang | A61N 5/103 600/1 |

OTHER PUBLICATIONS

Trnková, Petra et al.; "New Inverse Planning Technology for Image-Guided Cervical Cancer Brachytherapy: Description and Evaluation Within a Clinical Frame," Radiotherapy and Oncology 93 (2009) pp. 331-340.

* cited by examiner

*Primary Examiner* — Hoon Song
(74) *Attorney, Agent, or Firm* — Fitch, Even, Tabin & Flannery LLP

(57) ABSTRACT

A control circuit identifies (prior to optimizing a radiation-treatment plan) at least one angle (such as one or more gantry angles as correspond to an arc-therapy treatment platform) to provide one or more identified angles. The control circuit then optimizes a radiation-treatment plan with respect to a particular patient target volume by using the identified angle(s) as preferred angles as regards irradiating the patient target volume. Being "preferred," the radiation-treatment plan is thereby influenced (without being required) towards changing a rate of moving the gantry when traversing the preferred angle(s). For example, the plan can be biased towards slowing down movement of the gantry at such angles to thereby deliver a relatively greater amount of radiation to the patient target volume at the preferred angle.

11 Claims, 2 Drawing Sheets

METHOD AND APPARATUS FOR USING PREFERRED ANGLES WHEN IRRADIATING PATIENT TARGET VOLUMES

RELATED APPLICATION(S)

This application claims the benefit of U.S. Provisional application No. 61/784,110, filed Mar. 14, 2013, which is incorporated by reference in its entirety herein.

TECHNICAL FIELD

This invention relates generally to the therapeutic irradiation of a patient's target volume.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Many treatment plans provide for exposing the target volume to radiation from a number of different directions. Arc therapy, for example, comprises one such approach. In such a case it often becomes useful or necessary to also adjust various mechanical components (such as, for example, multi-leaf collimators) of the treatment system when moving the radiation source with respect to the target volume. A radiation-treatment plan therefore often provides information regarding useful or necessary adjustments to various mechanical components of the treatment system during such a treatment.

In some cases the radiation source moves along the gantry that typically defines an arc around the patient's target volume at a relatively constant speed. In other cases the radiation treatment plan may call for the movement of the radiation source to slow down (or possibly to speed up) from time to time to permit administering a greater (or lesser) amount of radiation to the target volume from a particular direction. Such changes to speed of movement are the result of whatever decisions the optimization process generally happens to derive in a particular instance and without any previous preferences in these regards one way or the other.

BRIEF DESCRIPTION OF THE DRAWINGS

The above needs are at least partially met through provision of the method and apparatus for using preferred angles when irradiating patient target volumes described in the following detailed description, particularly when studied in conjunction with the drawings, wherein.

Figure 1:
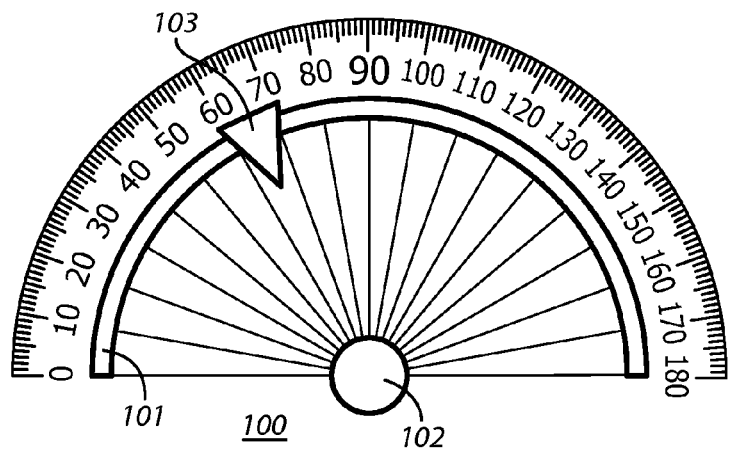
FIG. 1 comprises a side elevational schematic view as configured in accordance with the prior art.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit identifies (prior to optimizing a radiation-treatment plan) at least one angle (such as one or more gantry angles as correspond to an arc-therapy treatment platform) to provide one or more identified angles. The control circuit then optimizes a radiation-treatment plan with respect to a particular patient target volume by using the identified angle(s) as preferred angles as regards irradiating the patient target volume. Being "preferred," the radiation-treatment plan is thereby influenced towards changing a rate of moving the gantry when traversing the preferred angle(s). For example, the plan can be biased towards slowing down movement of the gantry at such angles to thereby deliver a relatively greater amount of radiation to the patient target volume at the preferred angle.

These teachings will accommodate identifying a range of contiguous angles to serve as the aforementioned identified angle(s). As a simple and non-limiting example in these regards, these teachings would accommodate identifying 15 degrees through 23 degrees as being the identified angle(s). So configured, and by way of a further non-limiting example, these teachings would then provide for permitting the optimizer to use that range of angles as a preferred part of the gantry path where slowing down passage of the radiation source is favored (though not mandated) in order to deliver a relatively greater radiation dosage as compared to other comparable portions of the gantry path where the radiation source moves more quickly.

So configured, an optimization process can leverage and otherwise take advantage of a technician's special experience and/or knowledge regarding one or more treatment angles that can be especially efficacious (either in general and/or with respect to the circumstances presented by a particular patient). By using such input to influence, without mandating, where the radiation source may slow its passage in order to deliver an increased amount of radiation these teachings effectively merge and fuse the best of two worlds—the power of optimization processes to test and compare a large number of possible treatment plans and the unique knowledge contributed (in general or in a specific instance) by an experienced practitioner.

By one approach the identification of the preferred angle can be based, in whole or in part, on objective and/or collective subjective standards. If desired, one can require the corresponding basis conform with standards of care and medical practices for the particular scenario for which the current treatment plan is being developed. For example, when developing a treatment plan for a breast, it may be preferred or required that the preferences come from a well-known authority within the community of radiation oncology for treating the breast or from a collective of radiation oncologists. These teachings will also accommodate basing such preferences on the wisdom and experience of the clinician who is designing the treatment plan who knows that a certain angle is preferable over other angles for a certain type of tumor or clinical presentation.

These and other benefits may become clearer upon making a thorough review and study of the following detailed description. For the sake of an illustrative (albeit non-limiting) example FIG. 1 offers a simple schematic representation of an arc-therapy radiation-treatment platform 100 where a gantry 101 partially surrounds a patient's target volume 102 (the latter typically being located at the isocenter of the machine) and where a radiation source 103 moves along the pathway defined by the gantry 101 to thereby direct radiation towards the patient target volume 102 from any of a variety of directions.

In this particular example the gantry forms a 180 degree pathway. The present teachings, however, are readily applied with systems having a lesser or greater number of degrees. These teachings are also useful in an application setting where the radiation source does not necessary move along a smoothly wholly-circular pathway.

For the sake of an example this description also presumes that the radiation source 103 moves under the control of a corresponding control system. In particular, the speed of the radiation source's 103 movement can be selectively controlled (and may be switched, for example, at least between a normal speed and a slower speed in addition to being selectively stopped) by the control system. Accordingly, when the radiation source 103 continues to source radiation (either continuously or pursuant to a regular, periodic pulsing of radiation), the radiation source 103 will deliver a greater amount of radiation over a given part of the gantry pathway when the radiation source 103 moves more slowly as compared to when it moves more quickly.

Figure 2:
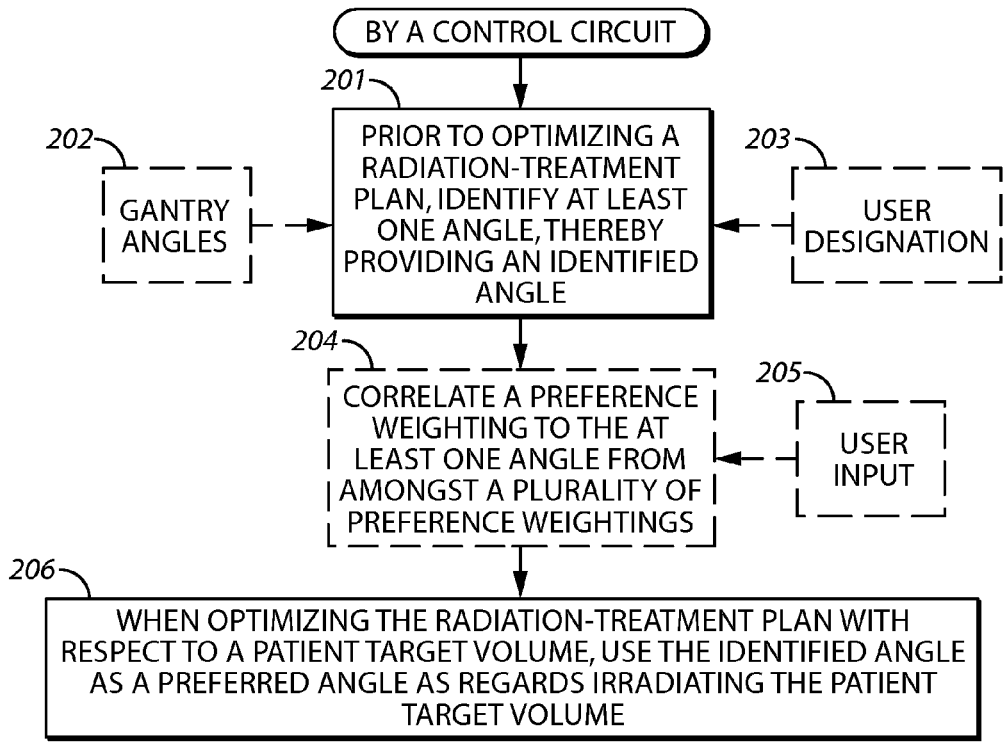
FIG. 2 comprises a flow diagram as configured in accordance with various embodiments of the invention.

Referring now to FIG. 2, an illustrative process 200 that is compatible with many of these teachings will now be presented. For the sake of an illustrative example it will be presumed that a control circuit of choice carries out this process 200. Examples in these regards are provided further herein.

Block 201 of this process 200 occurs prior to optimizing a radiation-treatment plan for a given specific patient target volume. (That said, it will be understood that, by one approach, these same teachings could be applied subsequent to when the optimization process has begun but prior to when the optimization process has concluded. Accordingly, this reference to "prior to optimizing" will be understood to refer to being prior to beginning the optimization process and also prior to concluding the optimization process.)

At block 201 the process 200 provides for identifying at least one angle to thereby provide an identified angle. For many application settings the identified angle will comprise a gantry angle (as denoted by reference numeral 202) as corresponds to an arc-therapy radiation-treatment apparatus as described above (and by way of a simple but non-exhaustive example, an angle of the radiation source with respect to the apparatus's isocenter as measured from the horizontal plan or other reference of choice). The information upon which to base such an identification can be drawn from one or more available sources including but not limited to the real-time entries of an available technician, a local database, and/or a remote database (such as an Internet-access server or the like).

Though these teachings will accommodate so identifying only a single such angle, in many cases this activity will comprise identifying a plurality of angles. That said, and notwithstanding that this process 200 may identify a plurality of angles, the so-identified plurality of angles will in any case be less than all of the available angles. Accordingly, and referring to the example of FIG. 1, the selected angles may comprise a plurality of the illustrated angles but will not constitute all 180 degrees-worth of available angles.

When identifying a plurality of angles these teachings will accommodate identifying the angles individually if desired (and to whatever resolution the user may wish). Accordingly, and by way of example, one group of identified angles could be expressed as 11 degrees, 12 degrees, 13 degrees, and so forth. As another example (and presuming a higher resolution view of the available angles), another group of identified angles could be expressed as 18.3 degrees, 18.4 degrees, 18.5 degrees, and so forth.

These teachings will also accommodate identifying a plurality of angles as a related series or range of angles when appropriate. Accordingly, and by way of example, one group of identified angles could be expressed as 11 degrees through 18 degrees. These examples are intended to serve only as illustrative examples and are not intended to suggest limitations as to how the identified angle or angles are "identified." For example, the identification of angles can also comprise identifying a particular arc sector or arc field as corresponds to the gantry geometry and preferred nomenclature.

As is detailed below, the identified angle(s) is then treated as a preferred angle when optimizing a corresponding radiation-treatment plan. By one approach there is only a single uniform preference level that applies. In such a case, an angle is either "preferred" or it is not. The weighting that the optimizer then accords that evinced preference is then commonly applied to all preferred angles.

By another approach, and as indicated at optional block 204, this process 200 will accommodate correlating a preference weighting to one or more of the aforementioned identified angles from amongst a plurality of preference weightings. This correlation may be in response to inputs from a user (as represented at block 205) and/or may result from the automatic application of one or more rules in these regards as comprises a part of the control circuit's programming.

The number of available preference weightings can vary as desired. There can be as few as two distinct preference weightings (that equate, for example, to a high preference and a normal or otherwise reduced preference as compared to the high preference) or there can be as many as ten, twenty, or even more such different preference weightings available for these purposes. When available, of course, the amount of preference to be observed by the optimizer can be selectively varied by using different preference weightings.

At block 206, this process 200 then provides for using the aforementioned identified angle(s) as a preferred angle(s) as regards irradiating the patient target volume when optimizing the radiation-treatment plan with respect to that patient target volume. Optimization in general comprise a well-understood area of endeavor and the precise manner in which a preference for one or more angles serves to influence and guide the optimization process can and will vary with the particular optimization approach being employed. Generally speaking, since optimization for a radiation-treatment plan such as an arc-therapy platform often proceeds on a field-by-field basis (which equates directly to an angle-by-angle view), modifying the optimization process to accommodate such a preference is well within the skills of the average person otherwise skilled in these arts. The ease by which this can be done is particularly exemplified by configuring the optimizer to specifically consider and test slowing down the movement of the radiation source when traversing the preferred angles (and not abandoning that approach too quickly) as one means of observing the aforementioned "preference."

Figure 3:
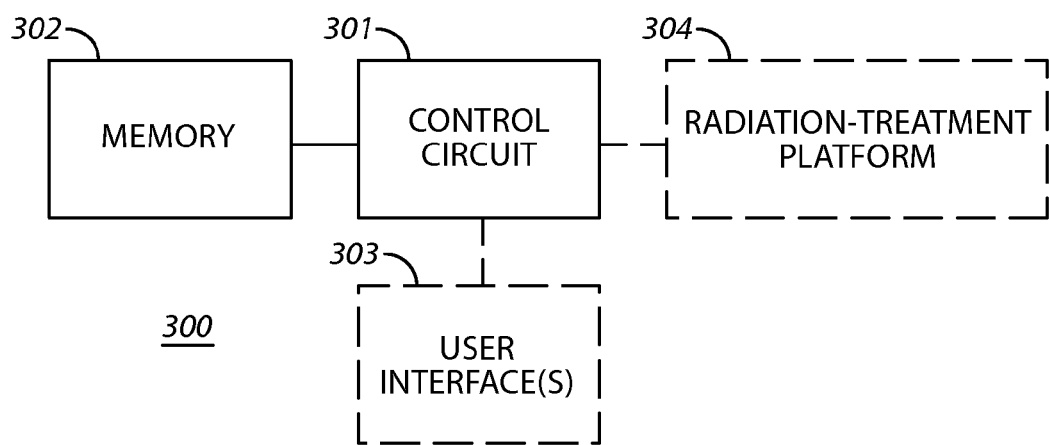
FIG. 3 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 3, an illustrative approach to such a platform 300 will now be provided.

In this example the enabling apparatus 300 includes a control circuit 301 that operably couples to a memory 302 and to an optional user interface 303. Such a control circuit 301 can comprise a fixed-purpose hard-wired platform or can comprise a partially or wholly programmable platform. These architectural options are well known and understood in the art and require no further description here. This control circuit 301 is configured (for example, by using corresponding programming as will be well understood by those skilled in the art) to carry out one or more of the steps, actions, and/or functions described herein.

The memory 302 may be integral to the control circuit 301 or can be physically discrete (in whole or in part) from the control circuit 301 as desired. This memory 302 can also be local with respect to the control circuit 301 (where, for example, both share a common circuit board, chassis, power supply, and/or housing) or can be partially or wholly remote with respect to the control circuit 301 (where, for example, the memory 302 is physically located in another facility, metropolitan area, or even country as compared to the control circuit 301).

This memory 302 can serve, for example, to non-transitorily store the computer instructions that, when executed by the control circuit 301, cause the control circuit 301 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The user interface 303 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

These teachings will also accommodate operably coupling the control circuit 301 to a radiation-treatment platform 304 (such as, by way of a non-limiting illustrative example, an arc-therapy radiation-treatment platform) of choice. So configured, the control circuit 301 can delivered the optimized radiation-therapy treatment plan to that platform 304 for use in treating the corresponding patient.

Such an apparatus 300 may be comprised of a plurality of physically distinct elements as is suggested by the illustration shown in FIG. 3. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, these teachings permit capturing and leveraging information regarding the particular and possibly unique efficacy of particular angles in the context of an optimization process. By conveying a non-mandatory preference (or range of preferences) for particular angles the optimization process can strongly consider such angles without ultimately being bound in those regards when a superior solution is otherwise available.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. As one example in these regards, it will be understood that the aforementioned preferred angles provide an opportunity in general to modulate the radiation more in any of a variety of ways. By way of one illustrative example, the increased time provided by slowing down the movement of the radiation source can also be used to further modify the aperture of a multi-leaf collimator and/or jaws and hence the shape of the radiation beam. In such a case, the amount of delivered radiation may remain the same (or even less) as compared to other non-preferred angles, but the extra time to modulate the beam can serve other purposes as well.

What is claimed is:

1. An apparatus comprising:
    a user interface;
    a control circuit operably coupled to the user interface and configured to:
        prior to optimizing an arc-therapy radiation-treatment plan, receiving input from a user via the user interface that identifies at least one angle that comprises a gantry angle as corresponds to an arc-therapy radiation-treatment apparatus as a preferred angle;
        when optimizing the arc-therapy radiation-treatment plan with respect to a patient target volume, using the identified at least one angle to modify the arc-therapy radiation-treatment plan to irradiate the patient target volume by, at least in part, permitting the arc-therapy radiation-treatment apparatus to slow down a rate of moving the gantry when traversing the preferred angle as compared to angles other than the preferred angle.

2. The apparatus of claim 1 wherein receiving input from a user via the user interface that identifies at least one angle comprises receiving input from a user via the user interface that identifies a plurality of angles, the plurality of angles being less than all of the available gantry angles that correspond to the arc-therapy radiation-treatment apparatus.

3. The apparatus of claim 1 wherein the control circuit is configured to slow down the rate of moving the gantry by slowing down movement of the gantry without stopping the gantry.

4. The apparatus of claim 1 wherein the control circuit is configured to correlate a preference weighting to the at least one angle from amongst a plurality of preference weightings.

5. The apparatus of claim 4 wherein the control circuit is configured to receive input from a user regarding the preference weighting.

6. The apparatus of claim 1 wherein the identified angle comprises at least one of:
an arc sector;
an arc field.

7. A method comprising:
by a control circuit that operably couples to a user interface:
prior to optimizing an arc-therapy radiation-treatment plan, receiving input from a user via the user interface that identifies at least one angle that comprises a gantry angle as corresponds to an arc-therapy radiation-treatment apparatus, thereby providing an identified angle;
when optimizing the arc-therapy radiation-treatment plan with respect to a patient target volume, using the identified angle as a preferred angle as regards irradiating the patient target volume by, at least in part, permitting the arc-therapy radiation-treatment apparatus to slow down a rate of moving the gantry when traversing the preferred angle as compared to angles other than the preferred angle.

8. The method of claim 7 wherein receiving input from a user via the user interface that identifies at least one angle comprises receiving input from a user via the user interface that identifies a plurality of angles, the plurality of angles being less than all of the available gantry angles that correspond to the arc-therapy radiation-treatment method.

9. The method of claim 7 wherein slowing down the rate of moving the gantry comprises slowing down movement of the gantry without stopping the gantry.

10. The method of claim 7 further comprising:
correlating a preference weighting to the at least one angle from amongst a plurality of preference weightings.

11. The method of claim 10 further comprising receiving input from a user regarding the preference weighting.

* * * * *